US00PP08052P

United States Patent [19]

van der Knaap

[11] Patent Number: Plant 8,052

[45] Date of Patent: Dec. 1, 1992

[54] CHRYSANTHEMUM PLANT—PUMA CULTIVAR

[75] Inventor: Jacques C. M. van der Knaap, DeLier, Netherlands

[73] Assignee: Fides Beheer B.V., DeLier, Netherlands

[21] Appl. No.: 680,137

[22] Filed: Apr. 3, 1991

[51] Int. Cl.[5] ..... A01H 5/00

[52] U.S. Cl. ..... Plt./77

[58] Field of Search ..... Plt./74, 74.1, 82.1, Plt./77, 76

*Primary Examiner*—Howard J. Locker

*Attorney, Agent, or Firm*—Burns, Doane, Swecker & Mathis

[57] ABSTRACT

A new and distinct cultivar of Chrysanthemum plant named Puma is provided. The new cultivar was the result of a controlled breeding program wherein an unnamed plant designated 86.2378 was pollinated by the Whisper cultivar (non-patented in the United States). More specifically, the new cultivar forms attractive relatively small white anemone-centered flowers having white ray florets and a green center when immature. The inflorescence tends to be pyramidal in configuration. The response period of the flowers is approximately eight weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium,* Ramat., and hereinafter is referred to by the cultivar name Puma.

The new cultivar is the product of a planned breeding program which had as its objective the creation of a new Chrysanthemum cultivar which exhibits attractive small white flowers having a green center when immature, exhibits a flower response period of approximately eight weeks, and possesses the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1987 at De Lier, The Netherlands. The female parent (i.e., the seed parent) was an unnamed plant designated 86.2378 and the male parent (i.e., the pollen parent) was the Whisper cultivar (non-patented in the United States). The parentage of the new cultivar can be summarized as follow:

86.2378 × Whisper.

The seeds resulting from the above pollination were sown and plantlets were obtained which were physically and biologically different from each other. Selective study resulted in the identification of a single plant of the new variety.

It was found that the new cultivar of the present invention:

(a) exhibits attractive relatively small anemone-centered flowers having an overall diameter of approximately 40 to 45 mm. wherein the ray florets are white and the flower center comprising the disc florets is approximately 22 mm. in diameter wherein the disc florets are green in coloration when immature, (b) bears flowers in a somewhat pyramidal configuration, (c) exhibits a flower response period of approximately eight weeks, and (d) has the ability to produce flowers of commercially acceptable quality throughout the year in a cut mum production program.

Asexual reproduction of the new cultivar by cuttings initially taken during January, 1988, as performed at De Lier, The Netherlands, in a controlled environment has demonstrated that the characteristics of the new cultivar as herein disclosed are firmly fixed and are retained through successive generations of asexual propagation.

Puma has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Majoor Bosshardt cultivar (U.S. plant patent application Ser. No. 07/680136, filed concurrently herewith), the following characteristics are observed:

| | PUMA | MAJOOR BOSSHARDT |
|---|---|---|
| Diameter of Flower: | Approximately 40 to 45 mm. | Approximately 60 to 65 mm. |
| Diameter of Disc: | Approximately 22 mm. | Approximately 17 mm. |
| Length of Petals: | Approximately 20 to 22 mm. | Approximately 30 to 35 mm. |
| Foliage Color: | Paler Green | Darker Green |
| Foliage Size: | Approximately 80 × 60 mm. | Approximately 80 × 70 mm. |
| Response: | Quicker | Slightly Slower |

Also at the harvest stage one can observe a disparity in the development of the petaloids at the flower center.

More specifically, such petaloid development is considerably greater in Puma than in Majoor Bosshardt.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during October, 1990. The plants described were grown under standard greenhouse conditions which approximate those commonly utilized for the production of cut mums.

Classification:

*Botanical.*—*Dendranthema morifolium* Ramat., cv. Puma.

*Commercial.*—Cut anemone spray.

INFLORESCENCE

A. Capitulum:

*Form.*—Pyramidal.

*Type.*—Anemone.

*Diameter across face.*—Approximately 40 to 45 mm. on average.

B. Corolla of ray and disc florets:

*Diameter across disc.*—Approximately 22 mm. on average.

*Length of petals.*—Approximately 20 to 22 mm. on average.

*Color (general tonality from a distance of three meters).*—White.

*Color ray florets (top surface).*—White Group 155D.

*Color disc florets.*—Yellow-Green Group 145A when immature changing to yellow when mature.

C. Reproductive organs:

*Androecium.*—Present in disc florets.

*Gynoecium.*—Present in disc florets.

PLANT

A. General appearance:

*Height.*—Approximately 100 cm. on average.

B. Foliage:

*Color (upper surface).*—Yellow-Green Group 147A.

*Color (under surface).*—Yellow-Green Group 137A.

*Size.*—Approximately 80×60 mm.

I claim:

1. A new and distinct cultivar of Chrysanthemum plant named Puma, substantially as herein shown and described, which:

(a) exhibits attractive relatively small anemone-centered flowers having an overall diameter of approximately 40 to 45 mm. wherein the ray florets are white and the flower center comprising the disc florets is approximately 25 mm. in diameter wherein the disc florets are green in coloration when immature, (b) bears flowers in a somewhat pyramidal configuration, (c) exhibits a flower response period of approximately eight weeks, and (d) has the ability to produce flowers of commercially acceptable quality throughout the year in a cut mum production program.

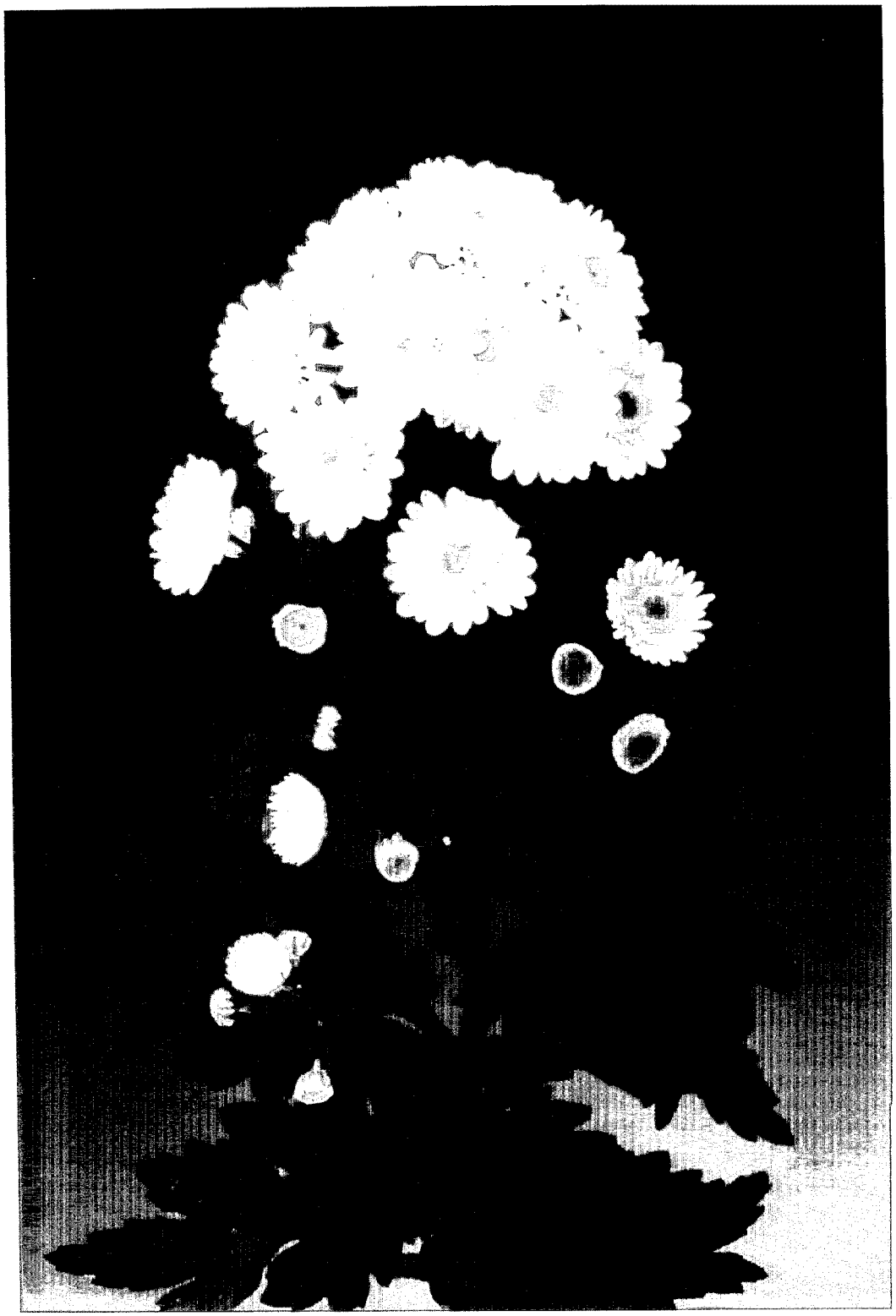

* * * * *